(12) United States Patent
Mizutani et al.

(10) Patent No.: US 7,811,434 B2
(45) Date of Patent: Oct. 12, 2010

(54) GAS SENSOR

(75) Inventors: Masaki Mizutani, Aichi (JP); Shigeki Mori, Seki (JP); Shigeo Kondo, Nagoya (JP); Nobuo Furuta, Kasugai (JP)

(73) Assignee: NGK Spark Plug Co., Ltd., Aichi (JP)

( * ) Notice: Subject to any disclaimer, the term of this patent is extended or adjusted under 35 U.S.C. 154(b) by 421 days.

(21) Appl. No.: 11/779,043

(22) Filed: Jul. 17, 2007

(65) Prior Publication Data

US 2008/0016942 A1 Jan. 24, 2008

(30) Foreign Application Priority Data

Jul. 18, 2006 (JP) .......................... P2006-195784

(51) Int. Cl.
*G01N 27/407* (2006.01)
(52) U.S. Cl. .................. 204/426; 204/428; 204/429; 204/424; 73/23.31
(58) Field of Classification Search ......... 204/424–429; 205/781, 783.5–785; 73/23.31, 23.32
See application file for complete search history.

(56) References Cited

U.S. PATENT DOCUMENTS 4,765,880 A * 8/1988 Hayakawa et al. .......... 204/425
5,238,551 A * 8/1993 Katsu et al. ................. 204/426

FOREIGN PATENT DOCUMENTS

| JP | 61-134655 A | 6/1986 |
| JP | 2001-242129 A | 9/2001 |
| JP | 2001-311714 A | 11/2001 |
| JP | 2002-107335 A | 4/2002 |

OTHER PUBLICATIONS

Human translation of JP61134655, 1986.*
Merriam-Webster Online Dictionary.*

* cited by examiner

*Primary Examiner*—Nam X Nguyen
*Assistant Examiner*—Susan Thai
(74) *Attorney, Agent, or Firm*—Sughrue Mion PLLC (57) ABSTRACT

A gas sensor including a gas detecting element extending in a longitudinal direction and in which a plurality of ceramic layers are stacked, and wherein a detecting portion is provided at a leading end side of the gas detecting element, the gas detecting element including: a first ceramic layer; a second ceramic layer; a first through-hole conductor; a first peripheral portion; a second through-hole conductor; a second peripheral portion; and an opening all as defined herein, wherein the first peripheral portion and the second peripheral portion respectively have mutually overlapping adhered portions and separated portions opposing one another through a gap continuing to the opening, and a relationship L1>S1 is satisfied, where L1 represents a maximum length of the adhered portion, and S1 represents a maximum length of the separated portion.

14 Claims, 10 Drawing Sheets

GAS SENSOR

BACKGROUND OF THE INVENTION

1. Field of the Invention

The present invention relates to a gas sensor having a stacked-type gas detecting element in which a plurality of ceramic layers are stacked.

2. Description of the Related Art

Conventionally, a plate-like gas detecting element is known which extends in a longitudinal direction. A plurality of ceramic layers are stacked to form a plate-like detecting element, and a detecting portion is formed at a leading end side thereof. Such gas detecting elements are disclosed, for example, in JP-A-61-134655, JP-A-2001-242129, JP-A-2001-311714 and JP-A-2002-107335. Through holes penetrating the ceramic layers are provided in the gas detecting element. In each of these through holes, a conductor is provided for electrically connecting a lead portion extending from a sensing electrode disposed in the interior of the gas detecting element and an electrode pad disposed on an outer surface of the gas detecting element.

Problems to be Solved by the Invention

Figure 9:
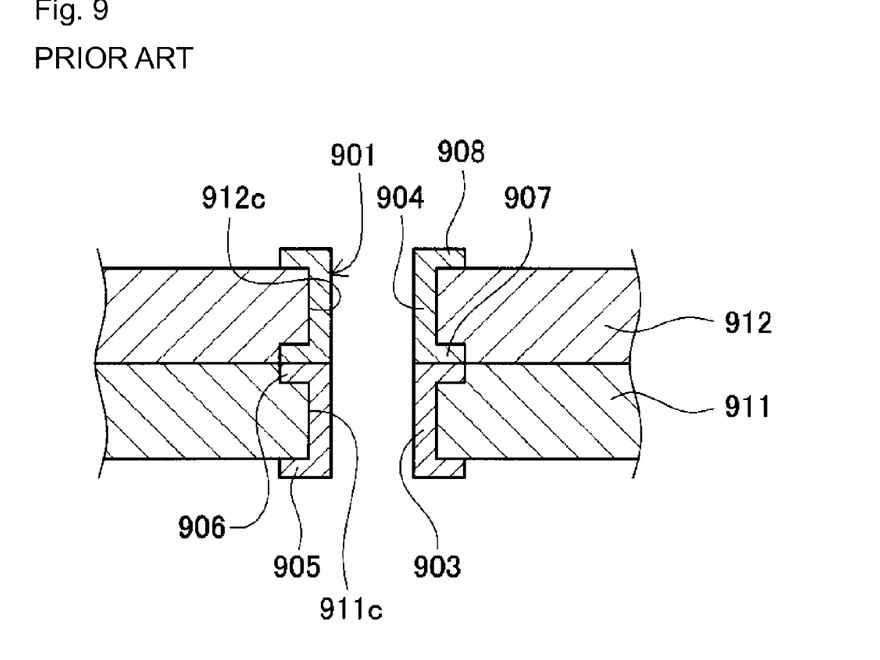
FIG. 9 is an explanatory diagram illustrating a schematic structure of an opening of a gas detecting element and vicinity thereof in accordance with the conventional art.
Figure 10:
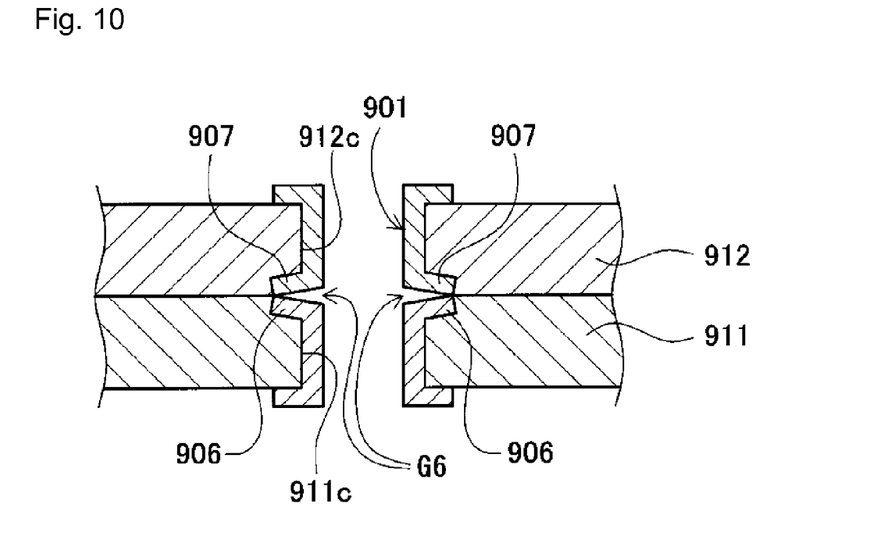
FIG. 10 is an explanatory diagram illustrating an opening where a gap is formed in the structure of FIG. 9 during sintering, and relates to a technical problem addressed by the present invention.
Figure 11:
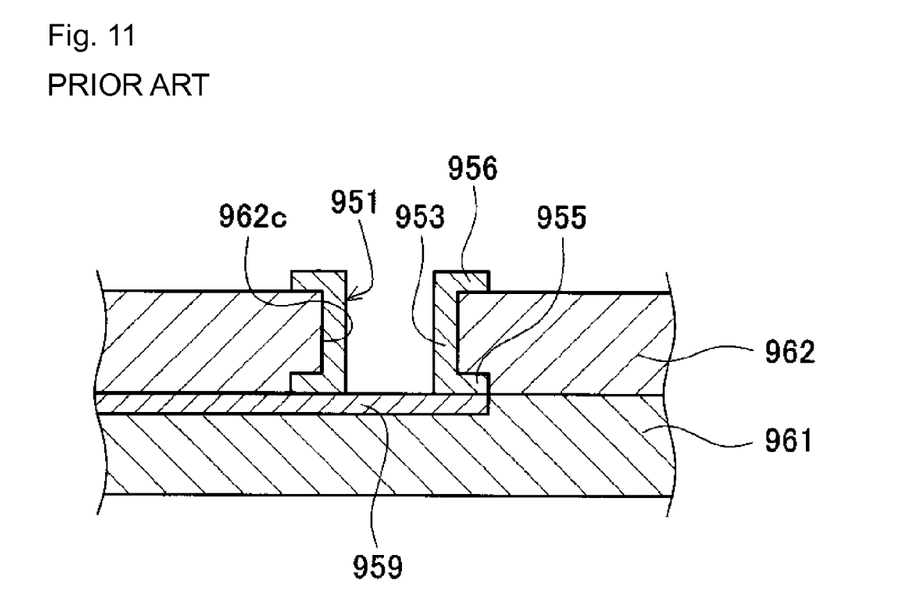
FIG. 11 is an explanatory diagram illustrating a schematic structure of a through hole of a gas detecting element and vicinity thereof in accordance with the conventional art.

FIGS. 9 to 12 discussed below relate to certain technical problems addressed by the present invention. FIGS. 9 and 11 represent conductor/ceramic opening and through hole structures conventionally found in plate-like gas detecting elements, whereas FIGS. 10 and 12 relate to technical problems associated with such structures newly discovered by the present inventors.

As shown in FIG. 9, among the aforementioned conductors, there is a type in which the conductors are provided on an inner peripheral surface of a connected through hole penetrating a plurality of ceramic layers, and an opening is provided therein. Such an opening 901 is generally fabricated as follows. Namely, unsintered through-hole conductors composed of an unsintered metallizing material, and which are formed into tubular through-hole conductors 903 and 904 after sintering, are formed on the inner peripheral surfaces of through holes 911c and 912c of ceramic green sheets corresponding to respective ceramic layers 911 and 912. In addition, unsintered peripheral portions, composed of the unsintered metallizing material and which are formed into annular peripheral portions 905, 906, 907 and 908 after sintering so as to be connected to the peripheries of respective both ends of the tubular through-hole conductors 903 and 904 in a surrounding manner, are respectively formed on the obverse and reverse surfaces of the ceramic green sheets.

Then, these ceramic green sheets are stacked. At this time, the unsintered through-hole conductors of the mutually overlapped ceramic green sheets abut one against another and the unsintered peripheral portions overlap one another. Subsequently, the stacked body of the unsintered ceramic is sintered, whereupon the peripheral portions 905, 906, 907 and 908 are formed from the unsintered peripheral portions, and the through-hole conductors 903 and 904 are formed from the unsintered through-hole conductors. Thus, the opening 901 formed by the inner peripheral surfaces of the conductors 903 and 904 is formed.

The amount of sintering shrinkage differs between the ceramic green sheet and the unsintered metallizing material. For this reason, as shown in FIG. 10, there are cases where a gap is produced between the mutually overlapping ceramic layers 911 and 912 at the peripheral portions of the through holes 911c and 912c during sintering due to this difference in sintering shrinkage. If such a gap occurs, a separated portion G6 is also produced between the mutually overlapping peripheral portions 906 and 907. As a result, the reliability of electrical connection between the through-hole conductors 903 and 904 can possibly suffer. This is because adhered portions where the peripheral portions 906 and 907 overlap become lost, or the adhered portions become extremely reduced, as shown in the drawing.

In another form, there is a type of conductor in which, as shown in FIG. 11, a through-hole conductor is provided on an inner peripheral surface of a single through hole, and an opening is formed therein. Such an opening 951 is generally fabricated as follows. Namely, an unsintered through-hole conductor, composed of an unsintered metallizing material and which is formed into a tubular through-hole conductor 953 after sintering, is formed on the inner peripheral surface of a through hole 962c of a ceramic green sheet corresponding to a ceramic layer 962. In addition, unsintered peripheral portions, composed of the unsintered metallizing material and which are formed into annular peripheral portions 955 and 956 after sintering so as to be connected to the peripheries of both ends of the through-hole conductor 953 in a surrounding manner, are respectively formed on the obverse and reverse surfaces of this ceramic green sheet. Meanwhile, an unsintered connection terminal, composed of the unsintered metallizing material and which is formed into a tabular connecting portion 959 after sintering, is formed on the obverse surface of a ceramic green sheet corresponding to a ceramic layer 961.

Then, these ceramic green sheets are stacked. At this time, the unsintered peripheral portion of one ceramic green sheet and the unsintered connection terminal of the other ceramic green sheet overlap one another. Subsequently, the stacked body of the unsintered ceramic is sintered, whereupon the through-hole conductor 953 is formed from the unsintered through-hole conductor, the peripheral portions 955 and 956 are formed from the unsintered peripheral portions, and the opening 951 is formed by the inner peripheral surface of the through-hole conductor 953. In addition, the connecting portion 959 is formed from the unsintered connection terminal.

Figure 12:
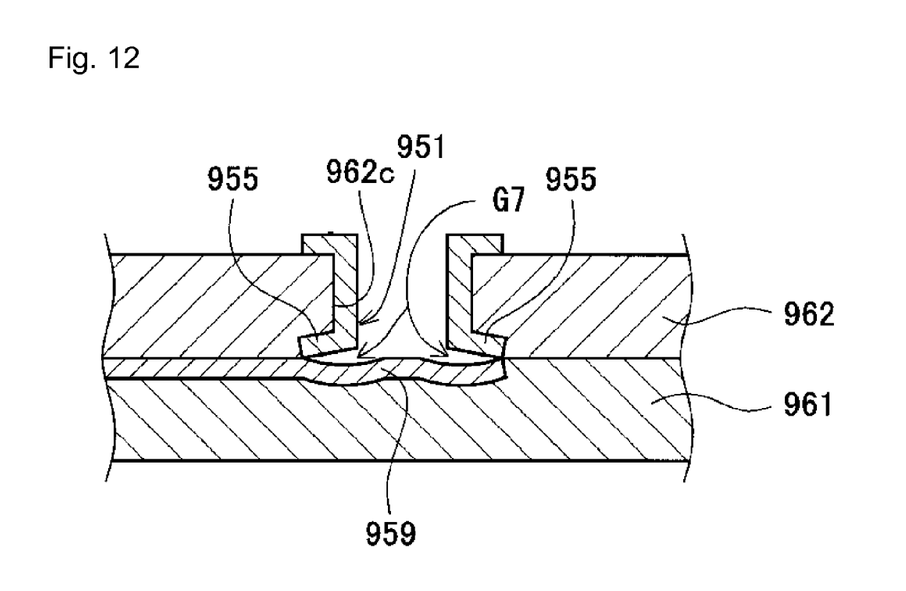
FIG. 12 is an explanatory diagram illustrating a through hole where a gap is formed in the structure of FIG. 10 during sintering, and relates to a technical problem addressed by the present invention.

In this case as well, since the amount of sintering shrinkage differs between the ceramic green sheet and the unsintered metallizing material, there are cases where a gap is produced between the mutually overlapping ceramic layers 961 and 962. Particularly, this gap is formed at the peripheral portion of the through hole 962c during sintering due to this difference in sintering shrinkage, as shown in FIG. 12. If such a gap occurs, separated portions G7 are also produced between the peripheral portion 955 and the connecting portion 959 overlapping one another. As a result, the reliability of electrical connection between the through-hole conductor 953 and the connecting portion 959 can possibly suffer. This is because adhered portions where the peripheral portion 955 and the connecting portion 959 overlap become lost, or the adhered portions become extremely reduced, as shown in the drawing.

The present invention has been made in view of the above-described circumstances, and an object thereof is to provide a gas sensor having a gas detecting element having both improved electrical connection reliability within a conductor and between the conductor and other conductors formed in the interior of the element.

SUMMARY OF THE INVENTION

The above object has been achieved, in accordance with a first aspect of the invention, by providing a gas sensor having a gas detecting element extending in a longitudinal direction and in which a plurality of ceramic layers are stacked, and wherein a detecting portion is formed at a leading end side thereof, the gas detecting element comprising: a first ceramic layer having a first surface and a second surface and having a first through hole penetrating therethrough (i.e., penetrating between the first surface and the second surface); a second ceramic layer having a first surface and a second surface and having a second through hole penetrating therethrough; a first through-hole conductor provided on an inner peripheral surface of the first through hole; a first peripheral portion provided on the second surface of the first ceramic layer at a periphery of the first through hole and connected to the first through-hole conductor; a second through-hole conductor provided on an inner peripheral surface of the second through hole; a second peripheral portion provided on the first surface of the second ceramic layer at a periphery of the second throughhole and connecting the second through-hole conductor and the first peripheral portion; and an opening formed by an inner peripheral surface of the first through-hole conductor and an inner peripheral surface of the second through-hole conductor, wherein the first peripheral portion and the second peripheral portion respectively have mutually overlapping adhered portions and separated portions opposing each other through a gap continuing to the opening, and wherein a relationship L1>S1 is satisfied, where L1 represents maximum length of the adhered portion, and S1 represents a maximum length of the separated portion.

According to the above-described aspect of the invention, since the first peripheral portion and the second peripheral portion are connected to one another by the adhered portion having a maximum length L1 greater than the maximum length S1 of the separated portion, the reliability of the electrical connection between the first through-hole conductor and the second through-hole conductor is high. Accordingly, a highly reliable gas sensor can be made. Furthermore, to further enhance the reliability of electrical connection, L1 is preferably set to not less than three times S1. In addition, the maximum length L1 of the adhered portion should preferably be set to from 60 μm to 200 μm.

The "gas sensor" of the invention may be embodied, for example, as an oxygen sensor, an air-fuel ratio sensor, an $NO_x$ sensor, a $CO_2$ sensor and the like, as long as the above-described requirements are satisfied.

In addition, the term "peripheral portion" means a through-hole conductor which is provided at a periphery of a through hole and is connected to a conductor provided in the through hole, and a circular shape, an elliptical shape, a rectangular shape, or the like can be selected as the shape of the peripheral portion.

Further, in the above-described gas sensor, the adhered portion, as viewed in the longitudinal direction, may be longer on a leading end side of the opening than on a base end side of the opening.

In a case where the gas detecting element has an elongated shape, a larger space can be secured in the longitudinal direction than in the widthwise direction. For this reason, the first peripheral portion and the second peripheral portion should preferably be formed into an elliptical or rectangular shape which is elongated in the longitudinal direction. In addition, the aforementioned opening is disposed on the base end side of the gas detecting element. Accordingly, if the longitudinal width of the adhered portion is made longer on the leading end side than on the base end side, the opening can be advantageously disposed closer to the base end of the gas detecting element.

Further, the above-described gas sensor may preferably further comprise: an electrode pad electrically connected to the first through-hole conductor and provided on an outer surface of the gas detecting element; and a connection terminal abutting against the electrode pad so as to be electrically connected to the electrode pad, wherein an abutment position between the connection terminal and the electrode pad is longitudinally offset from the first peripheral portion and the second peripheral portion.

In the portion where the first and second peripheral portions are located, the overall thickness of the gas detecting element increases by the thickness of the overlapping peripheral portions in some instances. Accordingly, if the connection terminal and the electrode pad abut immediately above the first and second peripheral portions, the connection reliability between them is possibly impaired. Accordingly, the abutment position between the connection terminal and the electrode pad is longitudinally offset from the first peripheral portion and the second peripheral portion, thereby making it possible to ensure connection reliability between the connection terminal and the electrode pad.

Particularly in the case where the longitudinal width of the adhered portion is set to be longer on the leading end side of the opening than on the base end side thereof, if the abutment position between the connection terminal and the electrode pad, as viewed in the longitudinal direction, is located more on the base end side than the opening, it is possible to easily ensure the connection reliability between the connection terminal and the electrode pad. In addition, according to the above-described structure, the abutment position between the connection terminal and the electrode pad can be easily set close to the opening, so that it is possible to enhance the degree of freedom of design. More preferably, the distance between the opening and the abutment position between the connection terminal and the electrode pad can be set in the range of 30 to 200 μm.

In addition, according to another aspect for attaining the above-described object, the present invention provides a gas sensor having a gas detecting element extending in a longitudinal direction and in which a plurality of ceramic layers are stacked, and wherein a detecting portion is provided at a leading end side thereof, the gas detecting element comprising: a first ceramic layer having a first surface and a second surface and having a first through hole penetrating therethrough (i.e., penetrating between the first surface and the second surface); a second ceramic layer having a first surface and a second surface and stacked on a side of the second surface of the first ceramic layer; a first through-hole conductor provided on an inner peripheral surface of the first through hole; a first peripheral portion provided on the second surface of the first ceramic layer at a periphery of the first through hole and connected to the first through-hole conductor; a second connecting portion provided on the first surface of the second ceramic layer and connected to the first peripheral portion so as to close the first through hole; and an opening formed by an inner peripheral surface of the first through-hole conductor, wherein the first peripheral portion and the second connecting portion respectively have mutually overlapping adhered portions and separated portions opposing each other through a gap continuing to the opening, and a relationship L2>S2 is satisfied, where L2 represents a maximum length of the adhered portion, and S2 represents a maximum length of the separated portion.

According to the above-described aspect of the invention, since the first peripheral portion and the second connecting portion are connected to one another by the adhered portion having a maximum length L2 greater than the maximum length S2 of the separated portion, the reliability of the electrical connection between the first through-hole conductor and the second through-hole conductor is high. Accordingly, a highly reliable gas sensor can be made. Furthermore, to further enhance the reliability of electrical connection, L2 is preferably set to not less than three times S2. In addition, the maximum length (maximum adhesion width) L2 of the adhered portion should preferably be 60 μm to 200 μm.

Further, in the above-described gas sensor, the adhered portion, as viewed in the longitudinal direction, may be longer on the leading end side of the opening than on the base end side of the opening.

In the case where the gas detecting element has an elongated shape, a larger space can be secured in the longitudinal direction than in the widthwise direction. For this reason, the third connecting portion and the first peripheral portion should preferably be formed into an elliptical or rectangular shape which is elongated in the longitudinal direction. In addition, the aforementioned opening is disposed on the base end side of the gas detecting element. Accordingly, if the longitudinal width of the adhered portion is made longer on the leading end side than on the base end side, the opening can be advantageously disposed closer to the base end of the gas detecting element.

The above-described gas sensor may preferably further comprise: an electrode pad electrically connected to the second through-hole conductor and provided on an outer surface of the gas detecting element; and a connection terminal abutting the electrode pad so as to be electrically connected to the electrode pad, wherein an abutment position between the connection terminal and the electrode pad is longitudinally offset from the second connecting portion and the first peripheral portion.

In the portion where the first peripheral portion and the second connecting portion are located, the overall thickness of the gas detecting element increases by the thickness of the overlapping peripheral portions in some cases. Accordingly, if the connection terminal and the electrode abut immediately above the first peripheral portion and the second connecting portion, the connection reliability between them is possibly impaired. Accordingly, the abutment position between the connection terminal and the electrode pad is longitudinally offset from the first peripheral portion and the second connecting portion, thereby making it possible to ensure the connection reliability between the connection terminal and the electrode pad.

Particularly in the case where the longitudinal width of the adhered portion is set to be longer on the leading end side of the opening than on the base end side thereof, if the abutment position between the connection terminal and the electrode pad, as viewed in the longitudinal direction, is located more on the base end side than the opening, it is possible to easily ensure the connection reliability between the connection terminal and the electrode pad. In addition, according to the above-described structure, the abutment position between the connection terminal and the electrode pad can be easily set close to the opening, so that it is possible to enhance the degree of freedom of design. More preferably, the distance between the opening and the abutment position between the connection terminal and the electrode pad can be set in the range of 30 to 200 μm.

DESCRIPTION OF REFERENCE NUMERALS

Reference numerals used to identify various structural features in the drawings include the following.

100: oxygen sensor (gas sensor)
139: connection terminal
200: gas detecting element
200a: leading end of the gas detecting element
200b: base end of the gas detecting element
201: sensor portion
206: first opening
207: second opening
208: third opening
211: first solid electrolyte layer (fourth ceramic layer)
211h: throughhole
213: first electrode
215: second electrode
215e, 219: peripheral portion
221: second solid electrolyte layer (second ceramic layer)
221h1, 221h2: through hole (second through hole)
222, 229: peripheral portion (second peripheral portion)
223: third electrode
223c: connecting portion (second connecting portion)
224, 225c, 233e, 235e: peripheral portion
226, 227: through-hole conductor (second through-hole conductor)
231: insulating layer (third ceramic layer)
231h1, 231h2: through hole
233d, 235d: through-hole conductor
233f, 235f: connecting portion
241: protective layer (first ceramic layer)
241h1, 241h2, 241h3: through hole (first through hole)
243, 244, 245: electrode pad
247, 248, 249: peripheral portion (first peripheral portion)

251: heater portion
253: fifth ceramic layer (ceramic layer)
255: sixth ceramic layer (ceramic layer)
261: heater-use outer connection pad
271, 272, 273: through-hole conductor (first through-hole conductor)
C1, C2, C3, C4, C5: adhered portion
G1, G2, G3, G4, G5: separated portion
L1, L2: maximum length (width) of the adhered portion
S1, S2: maximum length (width) of the separated portion
t1, t2, t3: abutment position

DETAILED DESCRIPTION OF THE INVENTION

Referring now to the drawings, a detailed description will be given of an embodiment of the invention. However, the present invention should not be construed as being limited thereto.

Figure 1:
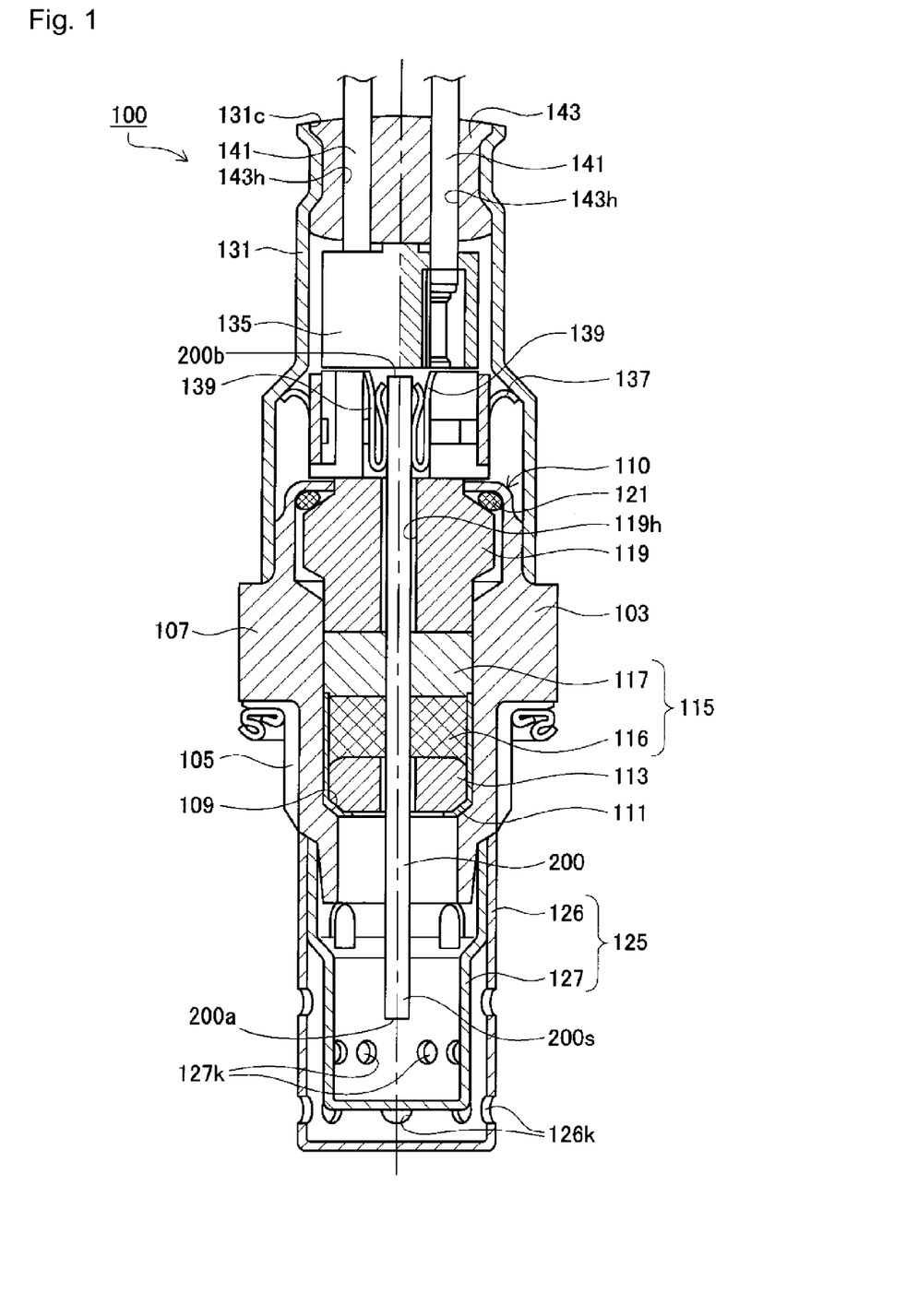
FIG. 1 is a longitudinal cross-sectional view of an oxygen sensor in accordance with an embodiment of the invention.

FIG. 1 shows an oxygen sensor (gas sensor) 100 in accordance with this embodiment. This oxygen sensor 100 is mounted on an exhaust pipe (not shown) of an automobile to detect the oxygen concentration in exhaust gas. In FIG. 1, the lower side of this oxygen sensor 100 is a leading end side, and the upper side thereof is a base end side. This oxygen sensor 100 comprises a gas detecting element 200, a cylindrical metal shell 103 for holding this gas detecting element 200 in its interior, a protector 125 fitted to a predetermined portion on the leading end side of this metal shell 103, and a cylindrical casing 131 connected to a predetermined portion on the base end side of this metal shell 103, among other structural components.

Figure 2:
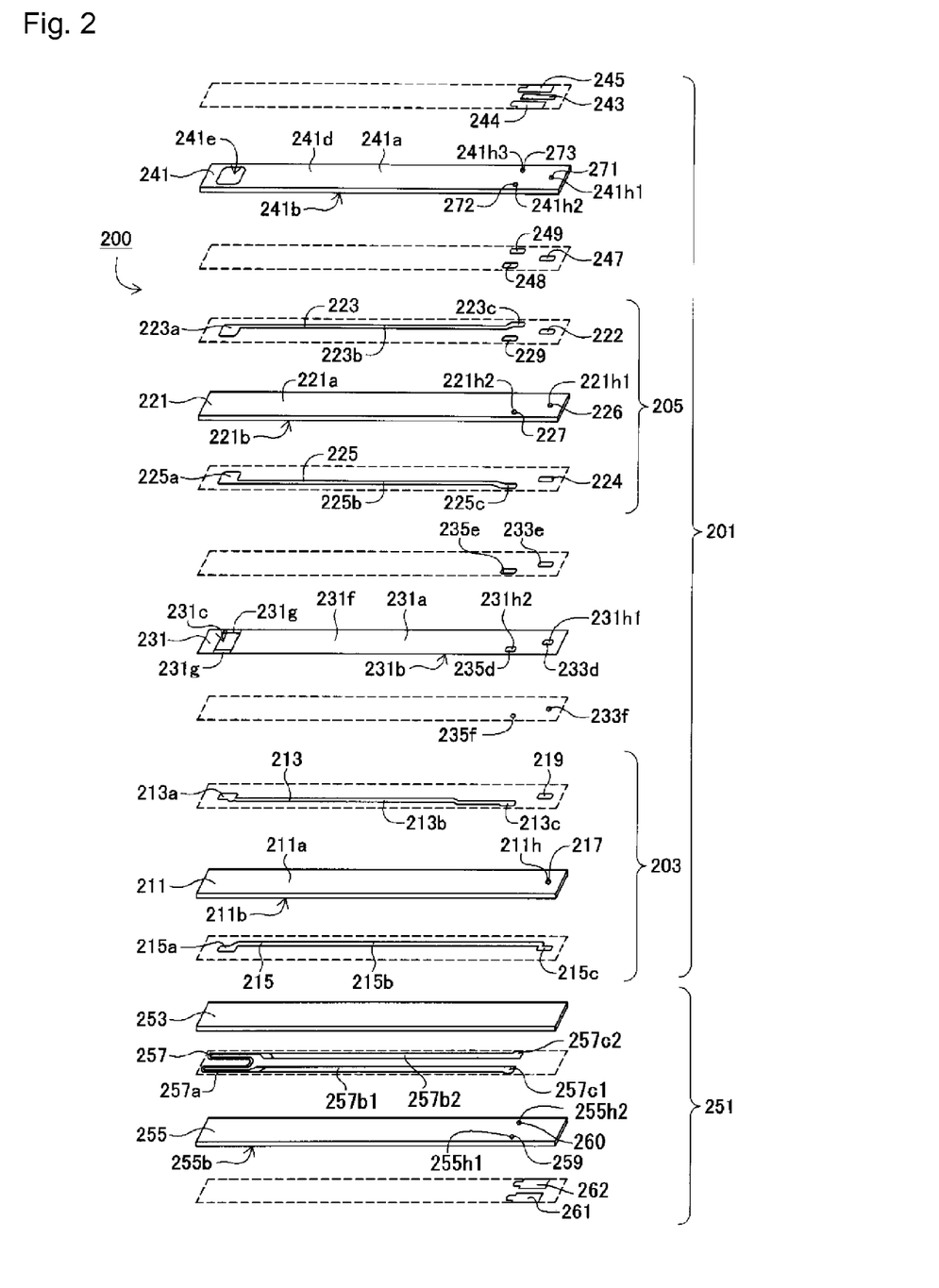
FIG. 2 is an exploded perspective view of a gas detecting element in accordance with the embodiment.

Of these, the gas detecting element 200 has a leading end 200a and a base end 200b, and is a rectangular plate-shaped stacked-type element in which a plurality of ceramic layers are stacked, its size being approx. 40 mm long, approx. 5 mm wide, and approx. 1.2 mm thick. As shown in the exploded perspective view of FIG. 2, this gas detecting element 200, when classified into its major components, includes a sensor portion 201 capable of sensing the oxygen concentration and a heater portion 251 capable of heating the sensor portion 201. In FIG. 2, the left side of this gas detecting element 200 is the leading end side, and the right side thereof is the base end side.

The sensor portion 201 has an oxygen concentration detection cell 203 and an oxygen pump cell 205.

The oxygen concentration detection cell 203 has a first solid electrolyte layer (fourth ceramic layer) 211 composed of a sintered compact of partially stabilized zirconia. A first electrode 213 is formed on an obverse surface 211a of this first solid electrolyte layer 211, and a second electrode 215 is formed on a reverse surface thereof The first electrode 213 includes of a first electrode portion 213a disposed on the leading end side, an elliptical connecting portion 213c disposed on the base end side and extending in the longitudinal direction of the gas detecting element 200, and a lead portion 213b connecting the first electrode portion 213a and the connecting portion 213c. Meanwhile, the second electrode 215 includes a second electrode portion 215a disposed on the leading end side, an elliptical peripheral portion 215c disposed on the base end side and extending in the longitudinal direction, and a lead portion 215b connecting the second electrode portion 215a and the peripheral portion 215c.

Figure 3:
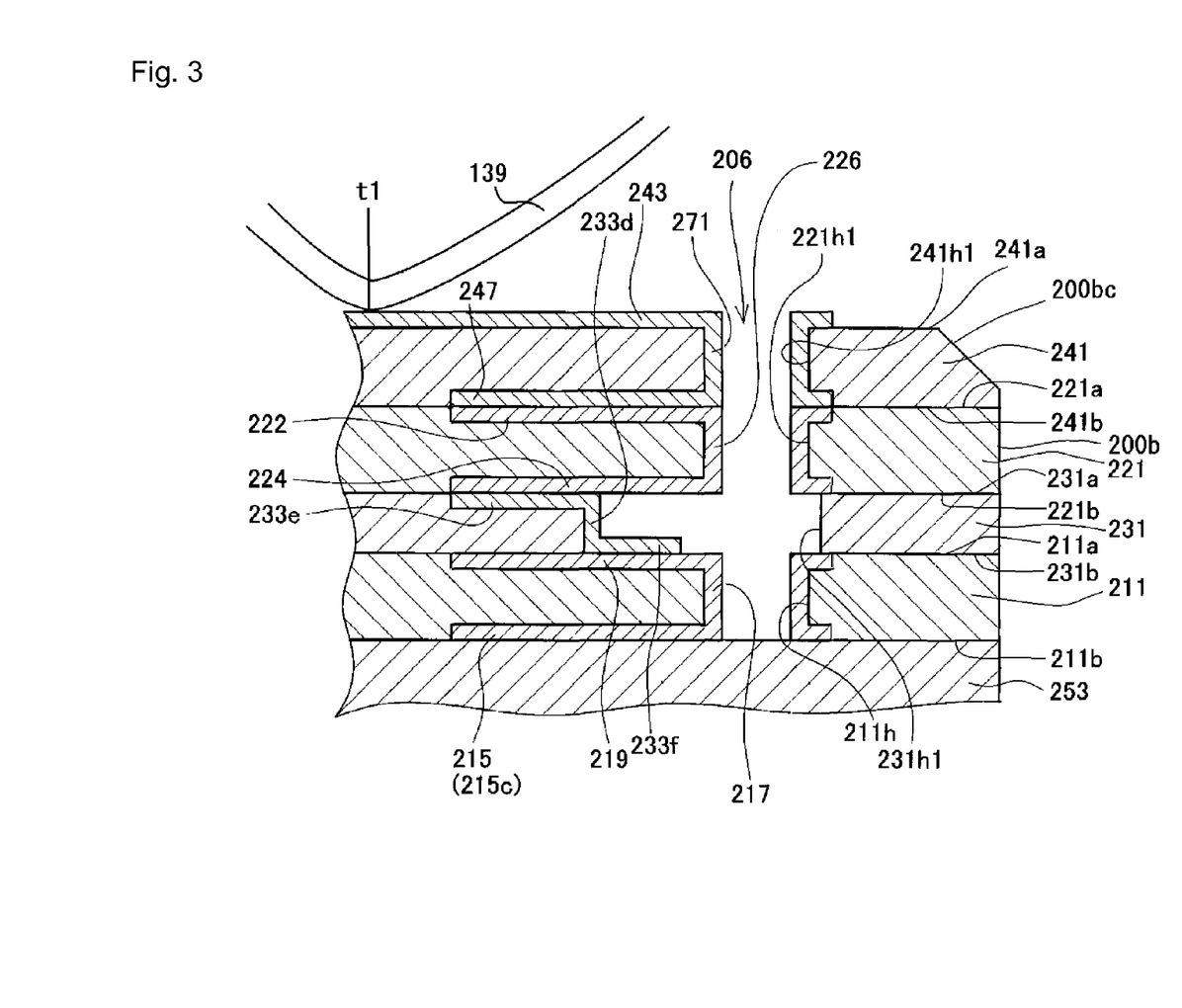
FIG. 3 is an explanatory diagram illustrating a schematic structure of a first opening 206 of the gas detecting element and vicinity thereof in accordance with the embodiment.

In addition, a through hole 211h is provided at a predetermined position on the base end side of the first solid electrolyte layer 211 (see also FIG. 3). Further, a tubular through-hole conductor 217 is formed on the inner peripheral surface of the through hole 211h. A peripheral portion 215c is provided on the reverse surface 211b at the periphery of the through hole 211h so as to connect to the through-hole conductor 217.

In addition, an elliptical peripheral portion 219 extending in the longitudinal direction is provided on the observe surface 211a of the first solid electrolyte layer 211 at the periphery of the through hole 211h so as to be connected to the through-hole conductor 217.

Next, a description will be given of the oxygen pump cell 205 (see FIG. 2). The oxygen pump cell 205 comprises a second solid electrolyte layer (second ceramic layer) 221 composed of a sintered compact of partially stabilized zirconia, a third electrode 223 formed on its obverse surface 221a, and a fourth electrode 225 formed on its reverse surface 221b. The third electrode 223 includes a third electrode portion 223a disposed on the leading end side, an elliptical peripheral portion (second connecting portion) 223c disposed on the base end side and extending in the longitudinal direction, and a lead portion 223b connecting the third electrode portion 223a and the peripheral portion 223c. Meanwhile, the fourth electrode 225 includes a fourth electrode portion 225a disposed on the leading end side, an elliptical peripheral portion 225c disposed on the base end side and extending in the longitudinal direction, and a lead portion 225b connecting the fourth electrode portion 225a and the peripheral portion 225c.

In addition, two through holes (second through holes) 221h1 and 221h2 are provided at predetermined positions on the base end side of the second solid electrolyte layer 221. In addition, elliptical peripheral portions (second peripheral portions) 222 and 229 extending in the longitudinal direction are provided on the obverse surface 221a of the second solid electrolyte layer 221 at the peripheries of the through holes 221h1 and 221h2. Meanwhile, elliptical peripheral portions 224 and 225c extending in the longitudinal direction are provided on the reverse surface 221b of the second solid electrolyte layer 221 at the peripheries of the through holes 221h1 and 221h2. Further, a tubular through-hole conductor 226 is formed on the inner peripheral surface of the through hole 221h1 so as to connect the peripheral portion 222 and the peripheral portion 224 (see FIG. 3). In addition, a tubular through-hole conductor (second through-hole conductor) 227 is formed on the inner peripheral surface of the through hole 221h2 so as to connect the peripheral portion 229 and the peripheral portion 225c (see FIG. 4).

Returning to FIG. 2, an insulating layer (third ceramic layer) 231 (having an obverse surface 231a and a reverse surface 231b) whose main constituent is alumina is stacked between the oxygen concentration detection cell 203 and the oxygen pump cell 205 described above. This insulating layer 231 includes an insulating portion 231f occupying a major portion thereof and a pair of porous diffusion rate controlling portions 231g disposed at predetermined positions on the leading end side. A gas measurement chamber 231c of a rectangular shape in plan view is penetratingly formed in the insulating layer 231 at a position corresponding to both the first electrode portion 213a of the oxygen concentration detection cell 203 and the fourth electrode portion 225a of the oxygen pump cell 205. This gas measurement chamber 231c communicates with the outside through the pair of diffusion rate controlling portions 231g at both widthwise end portions of the insulating layer 231. In this manner, the diffusion rate controlling portions 231g are able to control the diffusion at a time when detection gas flows into the gas measurement chamber 231c.

In addition, two elliptical through holes 231h1 and 231h2 extending in the longitudinal direction are formed on the base end side of the insulating layer 231. In addition, peripheral portions 233e and 235e are formed on the obverse surface 231a of the insulating layer 231 at the peripheries of the through holes 231h1 and 231h2. Additionally, connecting portions 233f and 235f are overlappingly provided on the peripheral portion 219 and the connecting portion 213c which are respectively exposed in the through holes 231h1 and 231h2. Further, a through-hole conductor 233d whose cross section is U-shaped is formed in the through hole 231h1 at a portion on the leading end side of its inner peripheral wall so as to connect the peripheral portion 233e and the connecting portion 233f (see FIG. 3). Meanwhile, a through-hole conductor 235d whose cross section is U-shaped is formed also in the through hole 231h2 at a portion on the leading end side of its inner peripheral wall so as to connect the peripheral portion 235e and the connecting portion 235f (see FIG. 4 also).

Returning to FIG. 2, a description will be given of a protective layer (first ceramic layer) 241. The protective layer 241 whose main constituent is alumina is stacked on the obverse surface 221a of the second solid electrolyte layer 221. This protective layer 241 includes a porous electrode protecting portion 241e disposed in correspondence with the third electrode portion 223a as well as a reinforcing portion 241d occupying the remaining portion. The electrode protecting portion 241e covers the third electrode portion 223a to prevent and suppress poisoning. In addition, the reinforcing portion 241d covers and protects the second solid electrolyte layer 221. A chamfered portion 200bc is formed at the base end of the protective layer 241.

In addition, three through holes (first through holes) 241h1, 241h2 and 241h3 are provided on the base end side of the protective layer 241. Three electrode pads 243, 244 and 245, which extend in the longitudinal direction, are formed on the obverse surface 241a of the protective layer 241 at the peripheries of the through holes 241h1, 241h2 and 241h3 so as to be juxtaposed in the widthwise direction. Meanwhile, three elliptical peripheral portions (first peripheral portions 247, 248 and 249 extending in the longitudinal direction are formed on a reverse surface 241b of the protective layer 241 at the peripheries of the through holes 241h1, 241h2 and 241h3 in a juxtaposed manner. Further, a through-hole conductor 271 is formed on the inner peripheral surface of the through hole 241h1 to connect the electrode pad 243 and the peripheral portion 247 (see FIG. 3). Additionally, a through-hole conductor 272 is formed on the inner peripheral surface of the through hole 241h2 to connect the electrode pad 244 and the peripheral portion 248 (see FIG. 4). Furthermore, a tubular through-hole conductor 273 is formed on the inner peripheral surface of the through hole 241h3 to connect the electrode pad 245 and the peripheral portion 249 (see FIG. 5).

Three openings 206, 207 and 208 are formed in the sensor portion 201 of the gas detecting element 200.

Of these, the first opening 206 is formed as the inner peripheral surfaces of the through-hole conductor 217, the through-hole conductor 233d, the through hole 231h1, the through-hole conductor 226, and the through-hole conductor 271 are connected in the thicknesswise direction (see FIG. 3). Meanwhile, the second opening 207 is formed as the inner peripheral surfaces of the through-hole conductor 235d, the through hole 231h2, the through-hole conductor 227, and the through-hole conductor 272 are connected in the thicknesswise direction (see FIG. 4). Further, the third opening 208 is formed by the inner peripheral surface of the through-hole conductor 273.

Next, returning to FIG. 2, a description will be given of the heater portion 251. The heater portion 251 includes a fifth ceramic layer 253 and a sixth ceramic layer 255 whose main constituent is alumina; a heating element 257 sandwiched between these ceramic layers; and a pair of heater-use outer connection pads 261 and 262 provided on the base end side of a reverse surface 255b of the second ceramic layer 255. The heating element 257 includes a heating portion 257a located on the leading end side; a pair of connecting portions 257c1 and 257c2 located on the base end side; and a pair of lead portions 257b1 and 257b2 for connecting the heating portion 257a and the connecting portions 257c1 and 257c2, respectively. In addition, the sixth ceramic layer 255 has through holes 255h1 and 255h2 on the base end side. A pair of conductors 259 and 260 are respectively provided on the inner peripheral surfaces of the through holes 255h1 and 255h2 so as to electrically connect the connecting portions 257c1 and 257c2 and the heater-use outer connection pads 261 and 262, respectively.

Next, returning to FIG. 1, a description will be given of the construction of other portions of the gas sensor 100. The metal shell 103 is formed of SUS 430, and has on its outer side an externally threaded portion 105 for installing the gas sensor 100 on the exhaust pipe as well as a hexagonal engaging portion 107 for engaging a tool during the installation. Further, an inner stepped portion 109 protruding radially inwardly is provided on the inner side of the metal shell 103. This inner stepped portion 109 supports a metal holder 111 for holding the gas detecting element 200. Further, a ceramic holder 113 and a talc filled layer 115 for locating the gas detecting element 200 in position are disposed on the inner side of this metal holder 111 sequentially from the leading end side. This talc filled layer 115 consists of two layers, a first talc filled layer 116 located on the leading end side and a second talc filled layer 117 located on the base end side. An alumina-made sleeve 119 is disposed on the base end side of the second talc filled layer 117. The sleeve 119 is formed into a multi-stage cylindrical shape, and the gas detecting element 200 is inserted into its axial hole 119h. A crimped portion 110 located on the base end side of the metal shell 103 is bent inwardly, thereby pressing the sleeve 119 toward the leading end side of the metal shell 103 by means of a stainless steel-made ring member 121.

In addition, the metallic protector 125 for covering a leading end portion 200s of the gas detecting element 200 projecting from the leading end of the metal shell 103 is welded to an outer periphery of the leading end of the metal shell 103. This protector 125 has a dual structure comprising a bottomed cylindrical outer protector 126 located on the outer side and a bottomed cylindrical inner protector 127 located on the inner side. A plurality of gas inlet holes 126k and 127k for respectively introducing the exhaust gases into the interior are provided in the outer protector 126 and the inner protector 127.

Meanwhile, the cylindrical casing 131 made of SUS 430 is welded to the base end side of the metal shell 103. A separator 135 is disposed on the inner side of the casing 131. The separator 135 is fixed to the casing 131 by means of a holding member 137 interposed between the separator 135 and the casing 131. In addition, a plurality of connection terminals 139 for electrically connecting to the gas detecting element 200, as well as a plurality of lead wires 141 whose one ends are electrically connected to these connection terminals 139 and which extend outside the base end side of the gas sensor 100, are disposed on the separator 135. In addition, a cylindrical rubber cap 143 for closing a base end-side opening 131c of the casing 131 is disposed on the base end side of the separator 135. The rubber cap 143 is fixed to the casing 131 by crimping the outer periphery of the casing 131 radially inwardly while being fitted to the casing 131. A plurality of insertion holes 143h are provided in the rubber cap 143, and the aforementioned plurality of lead wires 141 are respectively inserted therein.

Figure 5:
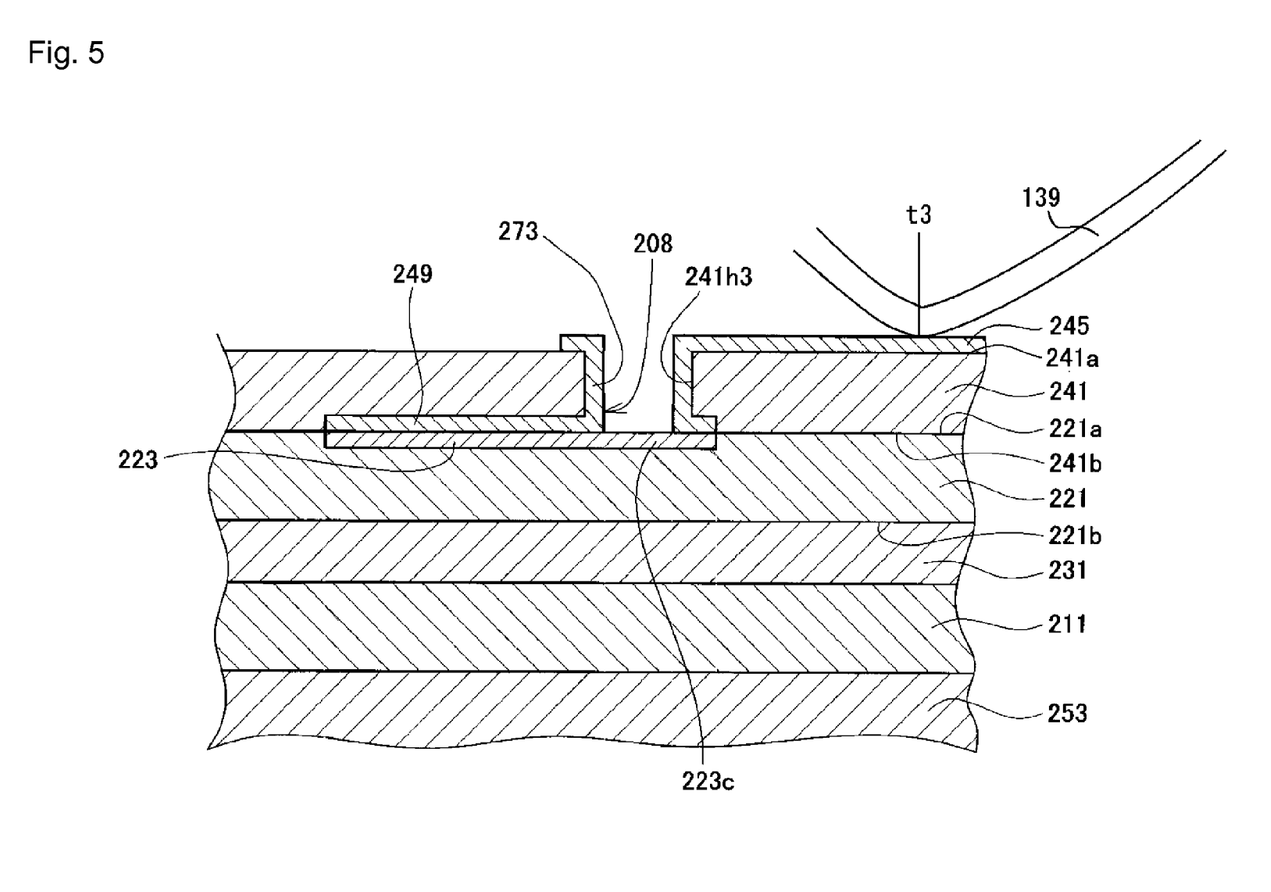
FIG. 5 is an explanatory diagram illustrating a schematic structure of an opening 208 of the gas detecting element and vicinity thereof in accordance with the embodiment.
Figure 6:
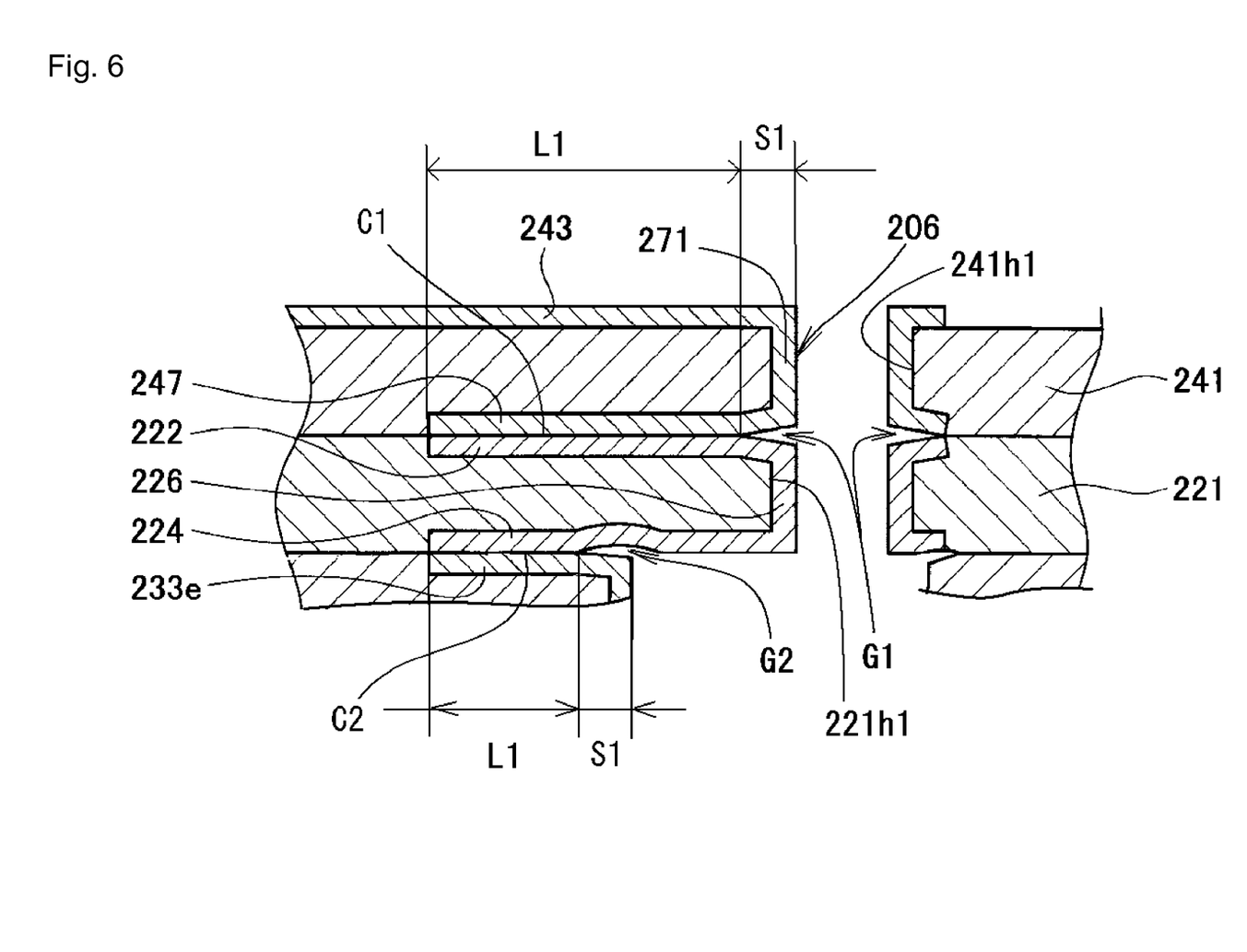
FIG. 6 is an explanatory diagram illustrating the first opening 206 where a gap is formed during sintering in the gas detecting element in accordance with the embodiment.
Figure 7:
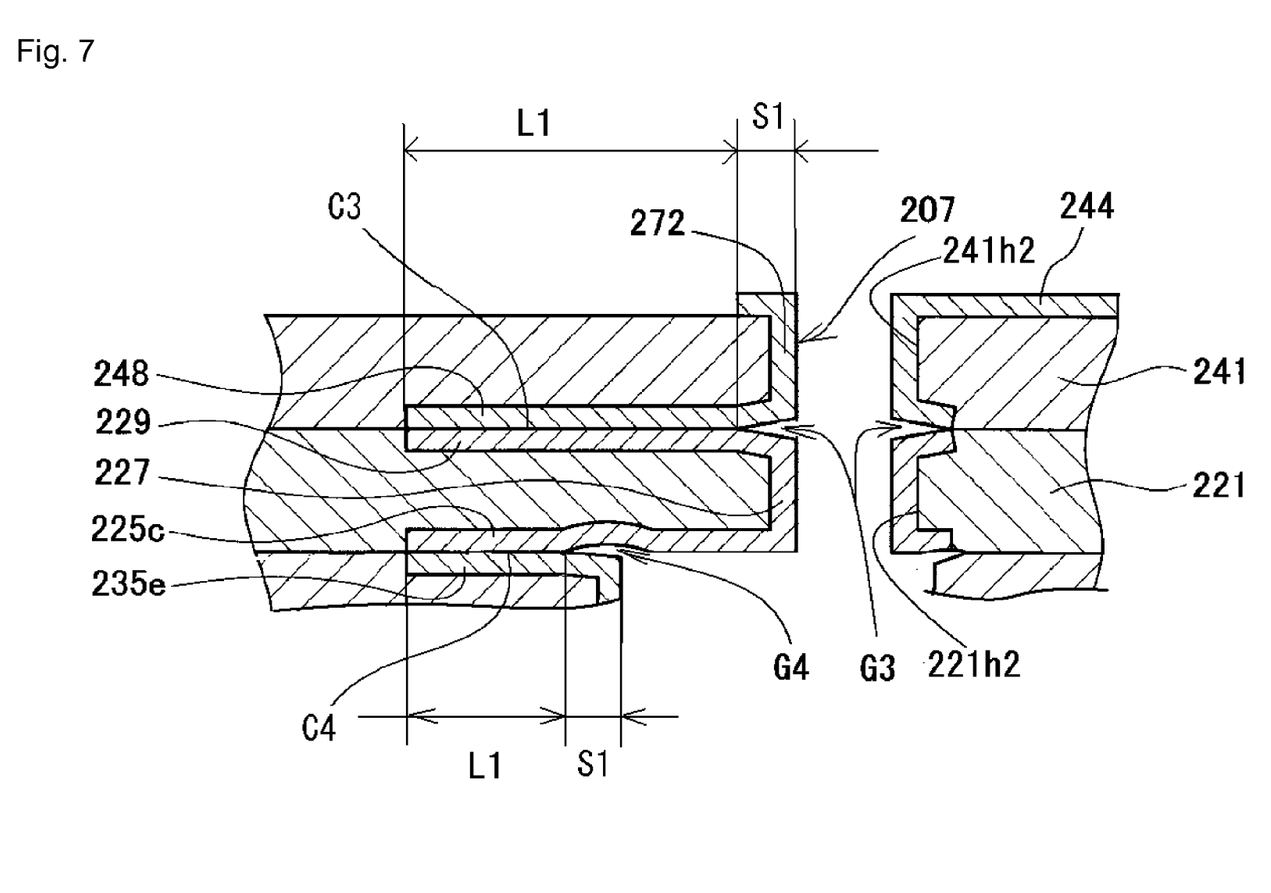
FIG. 7 is an explanatory diagram illustrating the second opening 207 where a gap is formed during sintering in the gas detecting element in accordance with the embodiment.
Figure 8:
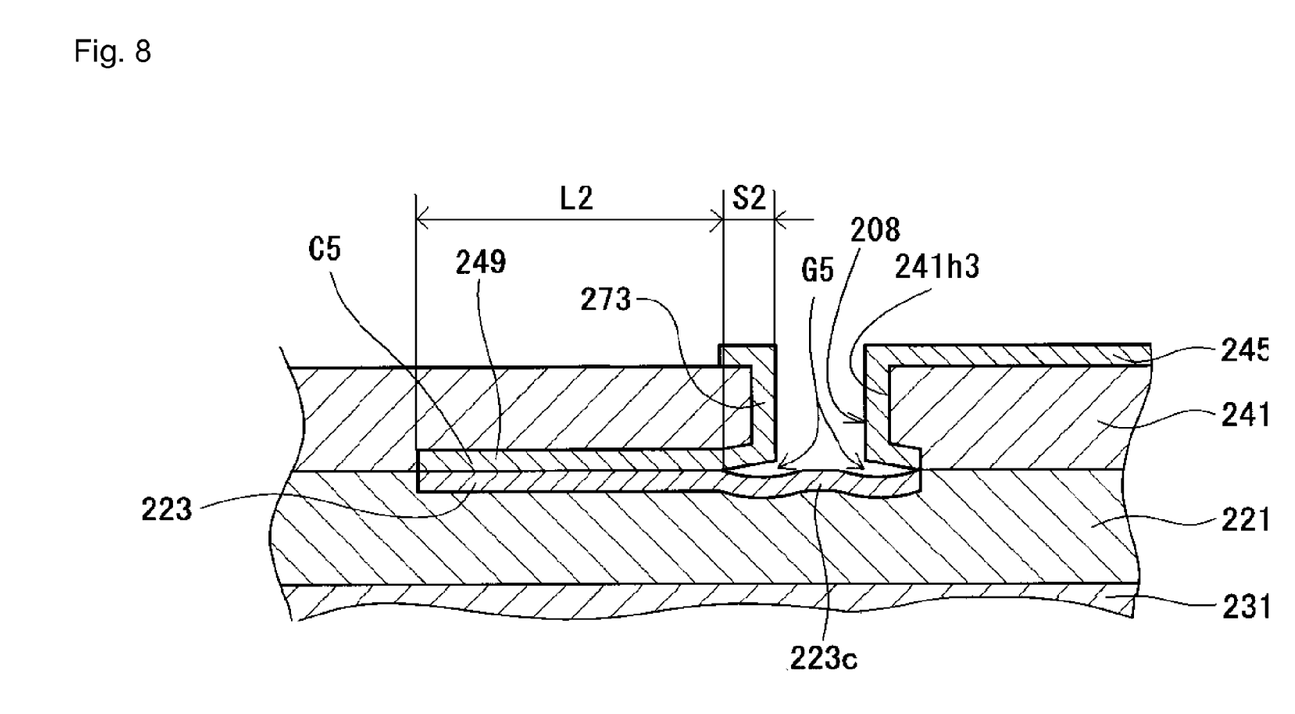
FIG. 8 is an explanatory diagram illustrating the opening 208 where a gap is formed during sintering in the gas detecting element in accordance with the embodiment.

Next, a description of specific structural portions of the invention will be given with reference to FIGS. 6 to 8. FIGS. 6 to 8 respectively correspond to FIGS. 3 to 5, and show the respective structural features in enlarged form. The gas detecting element 200 is formed by first forming an unsintered stacked body by a method such as a conventionally known sheet stacking technique and a conductor paste printing technique, and by subsequently simultaneously sintering the unsintered ceramic green sheet and a conductor paste whose main constituent is platinum and which has been formed between its layers and in the through holes by printing. At the time of sintering, there are cases where, in that portion of the mutually overlapped conductor paste which is adjacent to the through hole, the applied portions of the conductor paste peel off and a gap is produced. This occurs because the amount of sintering shrinkage differs between the ceramic green sheet and the unsintered metallizing material.

First, as shown in FIG. 6, separated portions G1 and G2, which are located adjacent to the first opening 206 and are respectively opposed to each other with a gap therebetween, are formed between the peripheral portion (first peripheral portion) 247 and the peripheral portion (second peripheral portion) 222 and between the peripheral portion 224 and the peripheral portion 233e which mutually overlap. In FIG. 3, the separated portions G1 and G2 are not shown.

However, even if the separated portions G1 and G2 are formed, the peripheral portion 247 and the peripheral portion 222 have mutually overlapping adhered portions C1, and the peripheral portion 224 and the peripheral portion 233e similarly have mutually overlapping adhered portions C2. Moreover, a maximum length L1 of the adhered portions C1 and C2 is set to be greater than a maximum length S1 of the separated portions G1 and G2. Accordingly, sufficient connection reliability is ensured between the peripheral portion 247 and the peripheral portion 222 and between the peripheral portion 224 and the peripheral portion 233e.

It should be noted that the adhered portion C1 is formed not only on the leading end side of the first opening 206 but also on the base end side thereof. However, in this embodiment, the width of the adhered portion C1 is set to be longer on the leading end side and very small on the base end side. As a result, as shown in FIG. 3, the first opening 206 can be set closer to the base end 200b of the gas detecting element 200. Specifically, the distance between the first opening 206 and the base end 200b is preferably set to be not greater than 3 mm. It should be noted that, in this embodiment, the distance between the first opening 206 and the base end 200b is set to be approximately 1.5 mm.

Because the first opening 206 is thus set close to the base end 200b, the electrode pad 243 is provided more on the leading end side than the first opening 206. As shown in FIG. 3, an abutment position t1 between the connection terminal 139 and the electrode pad 243 is located more on the leading end side than such as the peripheral portion 247 including the adhered portion C1. Namely, since the connection terminal 139 and the electrode pad 243 are in contact with one another at a portion which avoids an irregularity on the electrode pad 243 caused by the thickness portion of the peripheral portion 247 and the like, the connection reliability between the connection terminal 139 and the electrode pad 243 can be improved.

Figure 4:
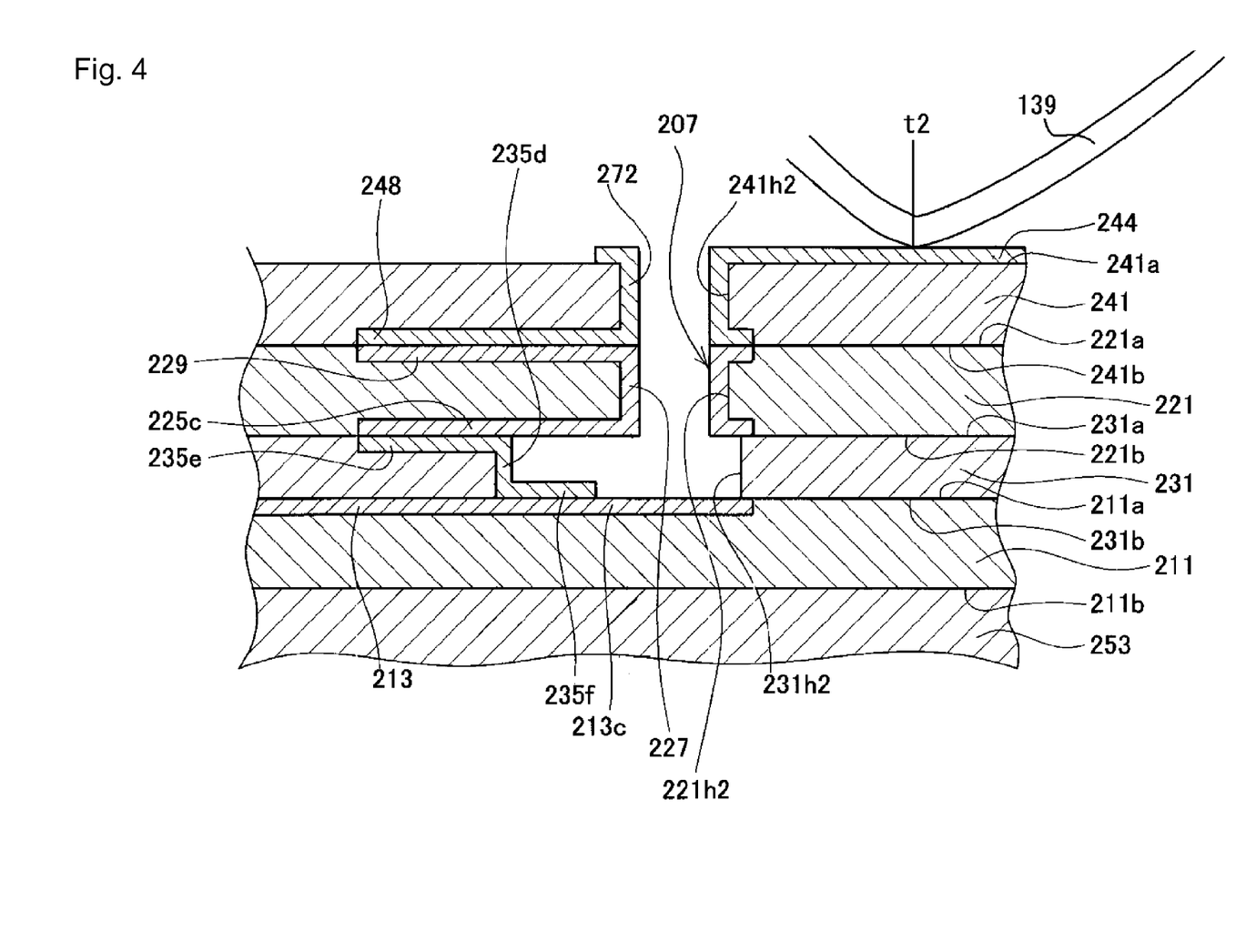
FIG. 4 is an explanatory diagram illustrating a schematic structure of a second opening 207 of the gas detecting element and vicinity thereof in accordance with the embodiment.

Next, as for the second opening 207, as shown in FIG. 7, separated portions G3 and G4, which are respectively opposed to one another with a gap therebetween, are formed between the peripheral portion (first peripheral portion) 248 and the peripheral portion (second peripheral portion) 229 and between the peripheral portion 225c and the peripheral portion 235e which mutually overlap. In FIG. 4, the separated portions G3 and G4 are not shown.

However, even if the separated portions G3 and G4 are formed, the peripheral portion 248 and the peripheral portion 229 have mutually overlapping adhered portions C3, and the peripheral portion 225c and the peripheral portion 235e similarly have mutually overlapping adhered portions C4. Moreover, a maximum length L1 of the adhered portions C3 and C4 is set to be greater than a maximum length S1 of the separated portions G3 and G4. Accordingly, sufficient connection reliability is ensured between the peripheral portion 248 and the peripheral portion 229 and between the peripheral portion 225c and the peripheral portion 235e.

As shown in FIG. 7, the adhered portion C3 is formed not only on the leading end side of the second opening 207 but also on the base end side thereof. However, in this embodiment, the width of the adhered portion C3 is set to be longer on the leading end side and very small on the base end side. Further, the electrode pad 244 is provided on the base end side of the second opening 207. As the abutment position t2 between the connection terminal 139 and the electrode pad 244 is thus located on the base end side where the adhered portion C3 is shorter (see FIG. 4), it becomes easy to avoid the irregularity occurring on the electrode pad 244 due to the thickness portion of the peripheral portion 248 and the like. In addition, the distance between the second opening 207 and the abutment position t2 can be made smaller than the distance between the first opening 206 and the abutment position t1. Specifically, the distance between the second opening 207 and the abutment position t2 is 180 μm, while the distance between the first opening 206 and the abutment position t1 is 220 μm.

Next, as for the third opening 208, as shown in FIG. 8, separated portions G5, which are opposed to one another with a gap therebetween, are formed between the peripheral portion (first peripheral portion) 249 and the connecting portion (second connecting portion) 223c which mutually overlap. In FIG. 5, the separated portions 5 are not shown.

However, even if the separated portions G5 are formed, the peripheral portion 249 and the peripheral portion 223c have mutually overlapping adhered portions C5. Moreover, a maximum length L2 of the adhered portions C5 is set to be greater than a maximum length S2 of the separated portions G5. Accordingly, sufficient connection reliability is ensured between the peripheral portion 249 and the peripheral portion 223. Consequently, it is possible to ensure reliability of the electrical connection between the through-hole conductor (first through-hole conductor) 237 and the connecting portion 223c.

As shown in FIG. 8, the adhered portion C5 is formed not only on the leading end side of the through hole (first through hole) 241h3 but also on the base end side thereof However, in this embodiment, the width of the adhered portion C5 is set to be longer on the leading end side and very small on the base end side. Further, the electrode pad 245 is provided on the base end side of the opening 208. As the abutment position t3 between the connection terminal 139 and the electrode pad 245 is thus located on the base end side where the adhered portion C5 is shorter (see FIG. 5), it becomes easy to avoid the irregularity occurring on the electrode pad 245 due to the thickness portion of the peripheral portion 249 and the like. In addition, the distance between the opening 208 and the abutment position t3 can be made smaller than the distance between the first opening 206 and the abutment position t1.

Specifically, the distance between the opening 208 and the abutment position t3 is 180 μm, while the distance between the first opening 206 and the abutment position t1 is 220 μm.

The aforementioned maximum lengths S1 of the separated portions G1 to G5 are 20 to 55 μm, respectively, while the maximum lengths L1 of the adhered portions C1 to C5 are 60 μm to 200 μm, respectively. The maximum lengths S1 of the adhered portions C1 to C5 are not less than three times the lengths of the separated portions G1 to G5, respectively.

In addition, the lengths of the peripheral portions 219, 224, 222, 225c, 229, 247, 248 and 249 are set to be greater on the leading end side than the lengths on the base end side by using their respective through holes as references. Specifically, their lengths on the leading end side are respectively 1.6 mm, and their lengths on the base end side are respectively 0.2 mm.

It should further be apparent to those skilled in the art that various changes in form and detail of the invention as shown and described above may be made. It is intended that such changes be included within the spirit and scope of the claims appended hereto.

This application is based on Japanese Patent Application JP 2006-195784, filed Jul. 18, 2006, the entire content of which is hereby incorporated by reference, the same as if set forth at length.

What is claimed is:

1. A gas sensor comprising a gas detecting element extending in a longitudinal direction and in which a plurality of ceramic layers are stacked, and wherein a detecting portion is provided at a leading end side of the gas detecting element, the gas detecting element comprising:
   a first ceramic layer having a first surface and a second surface and having a first through hole penetrating therethrough;
   a second ceramic layer having a first surface and a second surface and having a second through hole penetrating therethrough;
   a first through-hole conductor provided on an inner peripheral surface of the first through hole;
   a first peripheral portion provided on the second surface of the first ceramic layer at a periphery of the first through hole and electrically connected to the first through-hole conductor;
   a second through-hole conductor provided on an inner peripheral surface of the second through hole;
   a second peripheral portion provided on the first surface of the second ceramic layer at a periphery of the second through hole and electrically connecting the second through-hole conductor and the first peripheral portion; and
   an opening formed by an inner peripheral surface of the first through-hole conductor and an inner peripheral surface of the second through-hole conductor,
   wherein the first peripheral portion and the second peripheral portion have mutually overlapping adhered portions and separated portions opposing each other through a gap continuing to the opening, and
   a relationship L1>S1 is satisfied, where L1 represents a maximum length of the adhered portion, and S1 represents a maximum length of the separated portion.

2. The gas sensor as claimed in claim 1, wherein a relationship L1>3×S1 is satisfied.

3. The gas sensor as claimed in claim 1, wherein L1 is 60 to 200 μm.

4. The gas sensor as claimed in claim 1, wherein the adhered portion, as viewed in the longitudinal direction, is longer on a leading end side of the opening than on a base end side of the opening.

5. The gas sensor as claimed in claim 1, further comprising:
   an electrode pad electrically connected to the first through-hole conductor and provided on an outer surface of the gas detecting element; and
   a connection terminal abutting the electrode pad so as to be electrically connected to the electrode pad,
   wherein an abutment position between the connection terminal and the electrode pad is longitudinally offset from the first peripheral portion and the second peripheral portion.

6. The gas sensor as claimed in claim 5, wherein the abutment position between the connection terminal and the electrode pad, as viewed in the longitudinal direction, is located more on the base end side than the opening.

7. The gas sensor as claimed in claim 6, wherein a distance between the opening and the position of abutment between the connection terminal and the electrode pad is 30 to 200 μm.

8. A gas sensor comprising a gas detecting element extending in a longitudinal direction and in which a plurality of ceramic layers are stacked, and wherein a detecting portion is provided at a leading end side of the gas detecting element, the gas detecting element comprising:
   a first ceramic layer having a first surface and a second surface and having a first through hole penetrating therethrough;
   a second ceramic layer having a first surface and a second surface and stacked on a side of the second surface of the first ceramic layer;
   a first through-hole conductor provided on an inner peripheral surface of the first through hole;
   a first peripheral portion provided on the second surface of the first ceramic layer at a periphery of the first through hole and electrically connected to the first through-hole conductor;
   a second connecting portion provided on the first surface of the second ceramic layer and electrically connected to the first peripheral portion so as to close the first through hole; and
   an opening formed by an inner peripheral surface of the first through-hole conductor,
   wherein the first peripheral portion and the second connecting portion have mutually overlapping adhered portions and separated portions opposing each other through a gap continuing to the opening, and
   a relationship L2>S2 is satisfied, where L2 represents a maximum length of the adhered portion, and S2 represents a maximum length of the separated portion.

9. The gas sensor as claimed in claim 8, wherein a relationship L2>3×S2 is satisfied.

10. The gas sensor as claimed in claim 8, wherein L2 is 60 to 200 μm.

11. The gas sensor as claimed in claim 8, wherein the adhered portion, as viewed in the longitudinal direction, is longer on a leading end side of the opening than on a base end side of the opening.

12. The gas sensor as claimed in claim 8, further comprising:
   an electrode pad electrically connected to the first through-hole conductor and provided on an outer surface of the gas detecting element; and
   a connection terminal abutting the electrode pad so as to be electrically connected to the electrode pad,
   wherein an abutment position between the connection terminal and the electrode pad is longitudinally offset from the first peripheral portion and the second connecting portion.

13. The gas sensor as claimed in claim 12, wherein the abutment position between the connection terminal and the electrode pad, as viewed in the longitudinal direction, is located more on the base end side than the opening.

14. The gas sensor as claimed in claim 13, wherein a distance between the opening and the position of abutment between the connection terminal and the electrode pad is 30 to 200 μm.

* * * * *